US005707635A

United States Patent [19]

Deckner et al.

[11] Patent Number: 5,707,635
[45] Date of Patent: Jan. 13, 1998

[54] GEL TYPE COSMETIC COMPOSITIONS

[75] Inventors: George Endel Deckner, Trumbull; Brian Scott Lombardo, Ansonia, both of Conn.

[73] Assignee: Richardson-Vicks Inc., Shelton, Conn.

[21] Appl. No.: 249,093

[22] Filed: May 25, 1994

Related U.S. Application Data

[63] Continuation of Ser. No. 121,661, Sep. 15, 1993, abandoned, which is a continuation of Ser. No. 931,553, Aug. 18, 1992, abandoned, which is a continuation of Ser. No. 778,423, Oct. 16, 1991, abandoned.

[51] Int. Cl.$^6$ .................. A61K 31/07; A61K 7/00
[52] U.S. Cl. .............. 424/401; 424/59; 514/859; 514/844; 514/944; 514/725
[58] Field of Search ............ 424/59, 401, 70.17, 424/78.03, 63; 514/944, 859

[56] References Cited

U.S. PATENT DOCUMENTS

| 3,920,810 | 11/1975 | Rankin | 424/80 |
|---|---|---|---|
| 4,039,501 | 8/1977 | Babcock et al. | 260/30.4 R |
| 4,318,907 | 3/1982 | Kligman et al. | 424/230 |
| 4,355,028 | 10/1982 | Kligman et al. | 524/859 |
| 4,478,853 | 10/1984 | Chaussee | 424/59 |
| 4,540,568 | 9/1985 | Trager et al. | 424/81 |
| 4,599,379 | 7/1986 | Flesher et al. | 524/801 |
| 4,628,078 | 12/1986 | Glover et al. | 526/303.1 |
| 4,673,704 | 6/1987 | Flesher et al. | 524/519 |
| 4,704,436 | 11/1987 | Barabas | 525/326.9 |
| 4,731,242 | 3/1988 | Palinczar | 424/59 |
| 4,806,345 | 2/1989 | Bhattacharyya | 424/70 |
| 4,835,206 | 5/1989 | Farrar et al. | 524/457 |
| 4,837,019 | 6/1989 | Georgalas et al. | 424/101 |
| 4,849,484 | 7/1989 | Heard | 525/221 |
| 4,885,161 | 12/1989 | Cornell | 424/78 |
| 4,915,940 | 4/1990 | Saitoh et al. | 424/81 |
| 4,929,577 | 5/1990 | Cornell | 514/58 |
| 4,954,487 | 9/1990 | Cooper et al. | 514/159 |
| 5,009,969 | 4/1991 | Miller | 424/59 |
| 5,017,367 | 5/1991 | Stojkoski | 424/63 |
| 5,043,359 | 8/1991 | Ward et al. | 514/772 |
| 5,100,660 | 3/1992 | Hawe et al. | 424/78.35 |
| 5,221,530 | 6/1993 | Janchitraponveg et al. | 424/70 |
| 5,232,688 | 8/1993 | Ziegler et al. | 424/59 |
| 5,425,938 | 6/1995 | Znaiden et al. | 424/78.02 |

FOREIGN PATENT DOCUMENTS

| 067658 | 6/1982 | European Pat. Off. . |
|---|---|---|
| 228868 | 12/1986 | European Pat. Off. . |
| 312208 | 9/1988 | European Pat. Off. . |
| 67-2071745 | 6/1982 | Japan . |
| 57091913 | 3/1990 | Japan . |
| 2236760 | 10/1990 | United Kingdom . |
| 93/07902 | 4/1983 | WIPO . |
| 93/07903 | 4/1993 | WIPO . |

OTHER PUBLICATIONS

Sales Literature, Salcare SC92 for Cosmetic/Personal Care Applications, undated.
Sales Literature, Salcare SC91: The Cosmetic Formulator's Choice for Anionic Skin Care Products, undated.
Sales Literature, Sepigel 305, Thickening Agent for Aqueous Gels and Emulsions, undated.

*Primary Examiner*—Amy Hulina
*Attorney, Agent, or Firm*—Loretta J. Henderson; David K. Dabbiere

[57] ABSTRACT

A skin care composition in the form of a low pH aqueous gel. The compositions provide improved skinfeel and residue characteristics together with excellent moisturizing, emolliency, rub-in and absorption characteristics.

15 Claims, No Drawings

GEL TYPE COSMETIC COMPOSITIONS

This is a continuation of application Ser. No. 08/121,661, filed on Sep. 15, 1993, now abandoned, which is a continuation of application Ser. No. 07/931,553, filed on Aug. 18, 1992, now abandoned which is a continuation of application Ser. No. 07/778,423, filed on Oct. 16, 1991, now abandoned.

TECHNICAL FIELD

The present invention relates to cosmetic compositions. In particular it relates to stable low pH cosmetic compositions in the form of an aqueous gels which provide improved skinfeel and residue characteristics together with improved moisturizing, emolliency, rub-in and absorption characteristics.

BACKGROUND OF THE INVENTION

The treatment of human skin with various agents has been undertaken for many years with the goal being to keep the skin in a smooth and supple condition. Skin has the tendency to dry out when exposed to conditions of low humidity or to detergent solutions for extended periods. Skin is made up of several layers of cells which coat and protect the keratin and collagen fibrous proteins that form the skeleton of its structure. The outermost of these layer, referred to as the stratum corneum, is known to be composed of 250 A protein bundles surrounded by 80 A thick layers. Anionic surfactants and organic solvents typically penetrate the stratum corneum membrane and, by delipidization (i.e. removal of the lipids from the stratum corneum), destroy its integrity. This destruction of the skin surface topography leads to a rough feel and may eventually permit the surfactant or solvent to interact with the keratin, creating irritation.

It is now recognized that maintaining the proper water gradient across the stratum corneum is important to its functionality. Most of this water, which is sometimes considered to be the stratum corneum's plasticizer, comes from inside the body. If the humidity is too low, such as in a cold climate, insufficient water remains in the outer layers of the stratum corneum to properly plasticize the tissue; and the skin begins to scale and becomes itchy. Skin permeability is also decreased somewhat when there is inadequate water across the stratum corneum. On the other hand, too much water on the outside of the skin causes the stratum corneum to ultimately sorb three to five times its own weight of bound water. This swells and puckers the skin and results in approximately a two to three fold increase in the permeability of the skin to water and other polar molecules.

Conventional cosmetic cream and lotion compositions as described, for example, in Sagarin, *Cosmetics Science and Technology*, 2nd Edition, Volume 1, Wiley Interscience (1972) and *Encyclopedia of Chemical Technology*, Third Edition, Volume 7 are known to provide varying degrees of emolliency, barrier and water-retention (moisturizing) benefits. However, they can also suffer serious negatives in terms of skinfeel (i.e. they often feel very greasy on the skin) as well as having poor rub-in, absorption and residue characteristics. Other cosmetic compositions are disclosed in, for example, U.S. Pat. No. 4,837,019 to Georgalas et al., issued Jun. 16, 1989 and also in U.S. Pat. No. 4,863,725 to Deckner et al., issued Sep. 5, 1989, both of which are incorporated by reference herein. Further, it is desirable to deliver many cosmetic ingredients and pharmaceutical actives from low pH carriers; however, to date there have not been developed a suitable low pH vehicles. Also many pharmaceutical and cosmetic actives require a low pH environment for efficacy and/or stability. Current low pH vehicles contain natural gums and inorganic clays and powders and have not proved satisfactory. These systems exhibit poor stability and over-dry the skin and are cosmetically undesirable. i.e., have poor aesthetics.

Polyacrylic acids, e.g., carbomers, are well known for thickening cosmetic compositions; however these thickeners cannot be used at a low pH. Therefore, a great need exists for cosmetically elegant and stable low pH cosmetic compositions with a relatively high viscosity which can be used to deliver pharmaceutical and cosmetic actives.

Applicants have found that the use of specific polyacrylamides having high molecular weights in low pH cosmetic compositions provide excellent cosmetic benefits as well providing improved stability for low pH systems. Further high level of solvents such as alcohol and other water-soluble components which may be necessary to solubilize the active can be included in the compositions.

The present invention therefore provides low pH gel-type cosmetic compositions which are excellent carriers for certain low pH cosmetic ingredients and pharmaceutical actives and further have a high solvent tolerance.

The present invention also provides stable low pH gel-type cosmetic compositions which provide improvements in absorption, residue and skinfeel characteristics without detriment to either short or longer term moisturizing effectiveness or emolliency.

It is therefore an object of the present invention to provide improved cosmetic compositions which are excellent carriers for certain low pH cosmetic ingredients and pharmaceutical actives and which provide reduced tack and provide the user with a smoother skinfeel.

These and other objects of this invention will become apparent in light of the following disclosure.

SUMMARY OF THE INVENTION

Accordingly, the present invention provides a skin care composition in the form of an aqueous gel comprising: from about 0.05% to about 20% of a non-ionic polyacrylamide having a molecular weight of from about 1,000,000 to about 30,000,000 wherein said composition has a pH below about 4.

All percentages and ratios used herein are by weight and all measurements at 25° C. unless otherwise indicated.

DETAILED DESCRIPTION OF THE INVENTION

The low pH compositions of the present invention are formed from the combination of a non-ionic polymer and water where the pH is adjusted to a pH of below about 4, preferably below about 3.5 and most preferably below about 3.0. All levels and ratios are by weight of total composition, unless otherwise indicated. These compositions also have a high solvent tolerance, i.e., high level of solvents such as alcohol and other water-soluble components which may be necessary to solubilize the active can be included in the compositions.

Nonionic Polyacrylamide

The non-ionic polymers useful in the present invention are polyacrylamides and substituted polyacrylamides, branched or unbranched. These polymers are non-ionic water-dispersible polymers which can be formed from a variety of monomers including acrylamide and methacrylamide which are unsubstituted or substituted with one or two alkyl groups (preferably $C_1$–$C_5$). Preferred acrylate amides and methacrylate amides in which the amide nitrogen is unsubstituted, or substituted with one or two $C_1$–$C_5$ alkyl groups (preferably: methyl, ethyl or propyl), for example, acrylamide, methacrylamide, N-methylacrylamide, N-methylmethacrylamide, N,N-dimethylmethacrylamide, N-isopropylacrylamide, N-isopropylmethacrylamide and N,N-dimethylacrylamide. These monomers are generally disclosed in U.S. Pat. No. 4,963,348 to Bolich, Jr. et al., issued Oct. 16, 1990, incorporated by reference herein in its entirety. These copolymers may optionally be formed using conventional neutral crosslinking agents such as dialkenyl compounds. The use of such crosslinking agents for cationic polymers is disclosed in U.S. Pat. No. 4,628,078 to Glover et al. issued Dec. 9, 1986 and U.S. Pat. No. 4,599,379 to Flesher et al. issued Jul. 8, 1986 both of which are incorporated by reference herein. These non-ionic copolymers have a molecular weight greater than about 1,000,000 preferably greater than about 1,500,000 and range up to about 30,000,000. Preferably these non-ionic polyacrylamides are predispersed in a water-immiscible solvent such as mineral oil and the like, containing a high HLB surfactant (HLB from about 7 to about 10) which helps to facilitate water dispersibility of the polyacrylamide. Most preferred for use herein is the non-ionic polymer under the CTFA designation: polyacrylamide and isoparrafin and laureth-7, available as Sepigel from Seppic Corporation.

These non-ionic polyacrylamides are present at a level from about 0.05% to about 20%, preferably from about 0.5% to 10% and most preferably from about 1% to about 10%.

These compositions are preferably combined with a variety of optional ingredients. Most preferably, these gels are used as a carrier for pharmaceutical actives, most preferably anti-acne actives. The compositions of the present invention are most useful for those active ingredients which are acidic in nature or which require a low pH for optimal delivery or stability.

Pharmaceutical Actives

Pharmaceutical actives useful in the present invention include any chemical material or compound suitable for topical administration which induces any desired local or systemic effect. These actives are present at a level from about 0.1% to about 20%. Such agents include, but are not limited to ant-acne drugs, non-steroidal anti-inflammatory drugs, steroidal anti-inflammatory drugs, sunless tanning agents, sunscreen agents, wound healing agents, skin bleaching or lightening agents, antihistaminic drugs, antitussive drugs, antipruritic drugs, anticholinergic drugs, antiemetic and antinauseant drugs, anorexic drugs, central stimulant drugs, antiarrhythmic drugs, B-adrenergic blocker drugs, cardiotonic drugs, antihypertensive drugs, diuretic drugs, vasodilator drugs, vasoconstrictor drugs, anti-ulcer drugs, anesthetic drugs, antidepressant drugs, tranquilizer and sedative drugs, antipsychotic drugs, antimicrobial drugs, antineoplastic drugs, antimalarial drugs, muscle relaxant drugs, antispasmodic drugs, antidiarrheal drugs and bone-active drugs and mixtures thereof.

Also useful in the present invention are sunless tanning agents including dihydroxyacetone, glyceraldehyde, indoles and their derivatives, and the like. These sunless tanning agents may also be used in combination with conventional sunscreen agents such as those disclosed in Segarin, et al., at Chapter VIII, pages 189 et seq., of Cosmetics Science and Technology, incorporated by reference herein, as well as wound healing agents such as peptide derivatives, yeast, panthenol, lamin and kinetin.

Other useful skin actives include skin bleaching (or lightening) agents including but not limited to hydroquinone, ascorbic acid, kojic acid and sodium metabisulfite.

Most preferred drug actives are the anti-acne drugs. Anti-acne drugs preferred for use in the present invention include the keratolytics such as salicylcic acid, sulfur, lactic acid, glycolic, pyruvic acid, urea, resorcinol, and N-acetylcysteine; retinoids such as retinoic acid and its derivatives (e.g., cis and trans); antibiotics and antimicrobials such as benzoyl peroxide, octopirox, erythromycin, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate, and cholate.

Vitamins

Various vitamins may also be included in the compositions of the present invention. For example, ascorbic acid, panthothenic acid, Vitamin E, tocopherol and the like.

Water-soluble Humectant

These compositions can also contain one or more humectants/moisturizers. A variety of humectants/moisturizers can be employed and can be present at a level of from about 1% to about 30%, more preferably from about 2% to about 8% and most preferably from about 3% to about 5%. These materials include polyhydroxy alcohols such as sorbitol, glycerin, hexanetriol, propylene glycol, hexylene glycol and the like; polyethylene glycol; sugars and starches; sugar and starch derivatives (e.g. alkoxylated glucose); D-panthenol; hyaluronic acid; lactamide monoethanolamine; acetamide monoethanolamine; 2-pyrrolidone-5-carboxylic acid, and mixtures thereof.

Preferred humectants/moisturizers for use in the compositions of the present invention are the $C_3$–$C_6$ diols and triols. Especially preferred is the triol, glycerin. The compositions of this invention may also contain pharmaceutically acceptable optional components that modify the physical and/or therapeutic effects of the compositions. Such optional components may include, for example, additional solvents, emulsifiers, gelling agents, fragrances, preservatives, and stabilizers. Other useful humectants include glucosides (e.g., Glucam E10 and E20 available from Amerchol Corporation), lactamide monoethanolamine, and acetamide monoethanolamine.

Mixtures of these water-soluble humectants can also be used.

In the present invention the water-soluble humectant, is present at a level of from about 0.5% to about 20%, preferably from about 1% to about 10%, more preferably from about 4% to about 8% by weight of the composition.

Optional Hydrophilic Gelling Agent

The low pH gel compositions of the present invention may also contain an additional hydrophilic gelling agent (which is stable at a low pH) at a level preferably from about 0.05% to about 1%, more preferably from about 0.1% to about 1%. The gelling agent preferably has a viscosity (1% aqueous solution, 20° C., Brookfield RVT) of at least about 4000 cps, more preferably at least about 10,000 cps, and most preferably at least about 50,000.

Suitable hydrophilic gelling agents can generally be described as water-soluble or colloidally water-soluble polymers, and include cellulose ethers (e.g. hydroxyethyl cellulose, methyl cellulose), hydroxypropyl guar gum and xanthan gum. Also useful are clays such as hectorite (Veegum) and bentonite.

Emollients

The compositions of the present invention may also comprise at least one emollient (stable at low pH). Preferred emollients are volatile silicone oils, non-volatile emollients, and mixtures thereof. The compositions of the present invention more preferably comprise at least one volatile silicone oil which functions as a liquid emollient, or especially in a mixture of volatile silicone oils and non-volatile emollients. The term "volatile", as used herein, refers to those materials which have a measurable vapor pressure at ambient temperature.

Volatile silicone oils useful in the compositions of the present invention are preferably cyclic or linear polydimethylsiloxanes containing from about 3 to about 9, preferably from about 4 to about 5, silicon atoms. The following formula illustrates cyclic volatile polydimethylsiloxanes useful in the compositions disclosed herein:

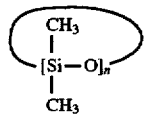

wherein n equals about 3 to about 7. Linear polydimethylsiloxanes contain from about 3 to about 9 silicon atoms per molecule and have the following general formula:

wherein n equals about 1 to about 7. Linear volatile silicone materials generally have viscosities of about 0.5 centistokes at 25° C. while cyclic materials typically have viscosities of less than about 10 centistokes. A description of various volatile silicone oils is found in Todd, et al., "Volatile Silicone Fluids for Cosmetics", *Cosmetics & Toiletries*, 91, pages 27-32 (1976), the disclosures of which are incorporated by reference herein in their entirety.

Examples of preferred volatile silicone oils useful herein include: Dow Corning 344, Dow Corning 345, and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The present compositions also preferably contain one or more non-volatile emollients. Such materials include hydrocarbons (e.g., the Permethyls), propoxylated alcohols, non-volatile silicone oils, and mixtures thereof. Emollients among those useful herein are described in 1 *Cosmetics Science and Technology* 27-104 (M. Balsam and E. Sagarin, Ed.; 1972), and U.S. Pat. No. 4,202,879, to Shelton, issued May 13, 1980 (both incorporated by reference herein).

Non-volatile silicone oils useful as an emollient material include polyalkylsiloxanes, polyalklyarylsiloxanes, and polyethersiloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include poly methylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Polysiloxane ethylene glycol ether copolymers are preferred copolymers for use in the present compositions.

The emollients typically comprise in total from about 2% to about 10%, and most preferably from about 2% to about 6% by weight of the compositions of the present invention.

A number of additional water-soluble materials can be added to the composition of the present invention, however. Such materials include the other humectants such as sorbitol, propylene glycol, ethoxylated glucose and hexanetriol; keratolytic agents such as salicylic acid; proteins and polypeptides and derivatives thereof; water-soluble or solubilizable preservatives such as Germall 115, methyl, ethyl, propyl and butyl esters of hydroxybenzoic acid, EDTA, Euxyl(RTM)K400, Bromopol (2-bromo-2-nitropropane-1, 3-diol), phenoxypropanol, DMDM Hydantoin/3-Iodo-2-Propynyl Butyl Carbamate (available as Glydant® and Glydant Plus®); anti-bacterials such as Irgasan (RTM) and phenoxyethanol (preferably at levels of from 0.5% to about 5%); soluble or colloidally soluble moisturizing agents such as hyaluronic acid, chitosan, and coloring agents; perfumes and perfume solubilizers etc. Water is also present at a level of from about 50% to about 99.3%, preferably from about 80% to about 95% by weight of the compositions herein.

Other Optional Components

A variety of additional ingredients may be added to the emulsion compositions of the present invention. These additional ingredients include various polymers for aiding the film-forming properties and substantivity of the formulation, preservatives for maintaining the antimicrobial integrity of the compositions, antioxidants, and agents suitable for anesthetic purposes such as fragrances, pigments, and colorings.

The compositions of the invention are in aqueous gel form and are preferably formulated so as to have product viscosity of at least about 4,000 and preferably in the range from about 4,000 to about 300,000 cps, more preferable from about 20,000 to about 200,000 cps and especially from about 80,000 to about 150,000 cps (20° C., neat, Brookfield RVT). Preferably the compositions are visually translucent. The compositions are also substantially free of oil, i.e. contain less than about 1%, and preferably less than about 0.1% of materials which are insoluble or which are not colloidallysoluble in the aqueous gel matrix at 10° C. "Colloidally-soluble" herein refers to particles in the usual colloidal size range, typically from 1 to 1000 nm, especially from 1 to 500 nm. In highly preferred embodiment, the compositions are substantially free of materials which are insoluble or not colloidally soluble in distilled water at 20° C. Such materials include many conventional emollient materials such as hydrocarbon oils and waxes, fatty alcohols, certain fatty alcohol ethers and sterols extracted from lanolin, beeswax derivatives, vegetable waxes, sterols and amides. The compositions can, however, contain low levels of insoluble ingredients added, for example for visual effect purposes, e.g., titianated mica.

These compositions may include additional co-solvents such as ethanol, isopropanol, butylene glycol, hexylene glycol, polyethylene glycol and polypropylene glycol.

The compositions of the invention have no need of additional surfactant materials which are conventionally added to cosmetic cream and lotion compositions in order to emulsify a water-in-soluble oily phase.

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLES

Example I

An anti-acne composition is made by combining the following components using conventional mixing technology.

| Ingredient | (% W/W) |
| --- | --- |
| Water, Purified | 54.0 |
| Alcohol SD 40 | 40.0 |
| Polyacrylamide and $C_{13-14}$ Isoparaffin and Laurath-7 | 4.0 |
| Salicylic Acid | 2.0 |

Water is added to a suitable size container. While mixing at a moderate speed (300 rpm), the polyquaternium-32 and mineral oil is added to the water. Separately, the alcohol is placed in a container and covered. Using a Lightnin' Mixer with a 3 blade paddle prop, the salicylic acid is added to the alcohol and mixed at a low speed (100 rpm) until all salicylic acid is dissolved. The alcohol is slowly added to the water phase to form a gel. The resulting gel is mixed at moderate speed until uniform.

The compositions display improved skinfeel and residue characteristics together with excellent moisturizing, emolliency, rub-in and absorption characteristics.

Example II

A sunless tanning composition is made by combining the following ingredients utilizing conventional mixing techniques as described above in Example I.

| Ingredient | (% W/W) |
| --- | --- |
| Water, Purified | 91.5 |
| Polyacrylamide and $C_{13-14}$ Isoparaffin and Laureth-7 | 3.0 |
| Dihydroxyacetone | 3.0 |
| Benzyl Alcohol | 0.5 |

Example III

An anti-acne composition is made by combining the following components as in Example I.

| Ingredient | (% W/W) |
| --- | --- |
| Water, Purified | 88.0 |
| Polyacrylamide and $C_{13-14}$ Isoparaffin and Laureth-7 | 2.0 |
| Benzoyl Peroxide | 10.0 |

Example IV

A topical analgesic composition is made by combining the following ingredients.

| Ingredient | (% W/W) |
| --- | --- |
| Water, Purified | 52.395 |
| Alcohol SD 40 | 40.000 |
| Polyacrylamide and $C_{13-14}$ Isoparaffin and Laureth-7 | 4.000 |
| Ibuprofen | 5.000 |
| Glycerin | 1.000 |
| Aloe Vera Gel | 0.500 |
| Menthol | 0.100 |
| Disodium EDTA | 0.005 |

The alcohol is added to a suitable size container. Using a Lightnin' mixer with a 3 blade paddle prop, the ibuprofen is added to the alcohol and mixed at low speed (100 rpm) until the ibuprofen is dissolved. Menthol is added to the alcohol and mixed until dissolved. Separately, water is added to a suitable size container. Aloe vera gel and disodium EDTA are added to the water and mixed at low speed (100 rpm) until completely dissolved. The water phase is then added to the alcohol phase and mixed until clear. Gylcerin is added and mixed until clear. While mixing at moderate speed (300 rpm), the polyacrylamide and $C_{13-14}$ isoparaffin and laureth-7 is added to form a gel. The resulting gel is mixed at moderate speed until uniform.

Example V

An anti-acne composition is made by combining the following components as in Example I with the pH adjusted to below about 4.0 with a solution of 10% citric acid.

| Ingredient | (% W/W) |
| --- | --- |
| Water, Purified | 87.5 |
| Polyacrylamide and $C_{13-14}$ Isoparaffin and Laureth-7 | 2.0 |
| Urea | 10.0 |
| Benzyl Alcohol | 0.5 |

Example VI

A moisturizing composition is made by combining the following components as in Example I.

| Ingredient | (% W/W) |
| --- | --- |
| Water, Purified | 93.5 |
| Polyacrylamide and $C_{13-14}$ Isoparaffin and Laureth-7 | 2.0 |
| Glycerin | 3.0 |
| Benzyl Alcohol | 0.5 |
| 2-pyrrolidone 5-Carboxylic Acid | 1.0 |

What is claimed is:

1. A skin care composition in the form of an aqueous gel comprising (a) from about 0.05% to about 20% of a nonionic crosslinked polyacrylamide having a molecular weight of from about 1,000,000 to about 30,000,000 and (b) from about 0.1% to about 20% of a compound selected from the group consisting of salicylic acid, sulfur, resorcinol, N-acetyl cysteine, octopirox, retinoids, benzoyl peroxide, erythromycin, tetracycline, azelaic acid, phenoxy ethanol, phenoxy propanol, ethyl acetate, clindamycin, meclocycline, flavinoids, lactic acid, glycolic acid, pyruvic acid, fumic acid, urea, scymnol sulfate, deoxycholate, cholate, and mixtures thereof, wherein said composition has a pH below 3.5.

2. A skin care composition according to claim 1 wherein the polyacrylamide comprises monomers selected from acrylamide and methacrylamide which are unsubstituted or substituted with a least one alkyl group having from about 1 to about 5 carbon atoms.

3. A skin care composition according to claim 2 wherein the polyacrylamide comprises monomers selected from the group consisting of acrylamide, methacrylamide, N-methacrylamide, N-methylmethacrylamide, N,N-dimethylmethacrylamide, N-isopropylacrylamide, N-isopropylmethacrylamide and N,N-dimethylacrylamide.

4. A skin care composition according to claim 1 wherein said composition further comprises a humectant.

5. A skin care composition according to claim 4 wherein said humectant is selected from the group consisting of polyhydroxy alcohols, glycerin, hexanetriol, propylene glycol, hexylene glycol, polyethylene glycol, 2-pyrrolidone-5-carboxylic acid, D-panthenol, hyaluronic acid, lactamide monoethanolamine, acetamide monoethanolamine and mixtures thereof.

6. A skin care composition according to claim 1 wherein said composition further comprises an emollient.

7. A skin care composition according to claim 6 wherein said emollient is a non-volatile silicone oil selected from the group consisting of polyalkylsiloxanes, polyalkylarylsiloxanes, and polyethersiloxane copolymers.

8. A skin care composition according to claim 1 wherein the compound (b) is selected from the group consisting of salicylic acid, sulfur, resorcinol, octopirox, retinoic acid and its derivatives, benzoyl peroxide, erythromycin, tetracyclin and mixtures thereof.

9. A skin care composition according to claim 1, wherein the compound (b) comprises salicylic acid.

10. A skin care composition according to claim 1, wherein the compound (b) comprises benzyl peroxide.

11. A skin care composition according to claim 1, wherein the compound (b) comprises retinoic acid.

12. A skin care composition according to claim 1, wherein the compound (b) comprises lactic acid.

13. A skin care composition according to claim 1, wherein the compound (b) comprises glycolic acid.

14. A skin care composition according to claim 1, wherein the compound (b) comprises a retinoid.

15. A skin care composition in the form of an aqueous gel comprising (a) from about 0.05% to about 20% of a nonionic crosslinked polyacrylamide having a molecular weight of from about 1,000,000 to about 30,000,000 and (b) from about 0.1% to about 20% of a compound selected from the group consisting of salicylic acid, sulfur, resorcinol, N-acetyl cysteine, octopirox, retinoids, benzoyl peroxide, erythromycin, tetracycline, azelaic acid, phenoxy ethanol, phenoxy propanol, ethyl acetate, clindamycin, meclocycline, flavinoids, lactic acid, glycolic acid, pyruvic acid, fumic acid, urea, scymnol sulfate, deoxycholate, cholate, and mixtures thereof, wherein said composition has a pH below about 3.0.

* * * * *

UNITED STATES PATENT AND TRADEMARK OFFICE
CERTIFICATE OF CORRECTION

PATENT NO.    :    5,707,635

DATED         :    January 13, 1998

INVENTOR(S)   :    George Endel Deckner et al.

It is certified that error appears in the above-identified patent and that said Letters Patent is hereby corrected as shown below:

At column 7, line 4 "water-in-soluble" should read --water-insoluble--.

At column 7, line 24 "Laurath-7$^1$" should read --Laureth-7$^1$--.

Signed and Sealed this

Second Day of June, 1998

Attest:

BRUCE LEHMAN

*Attesting Officer*        *Commissioner of Patents and Trademarks*